United States Patent [19]

Blom et al.

[11] Patent Number: 5,276,233

[45] Date of Patent: Jan. 4, 1994

[54] PROCESS AND CATALYST FOR PREPARING AROMATIC COMPOUNDS

[75] Inventors: Niels J. Blom, Hillerod, Denmark; Eric G. Derouane, Namur, Fed. Rep. of Germany

[73] Assignee: Haldor Topsee A/S, Denmark

[21] Appl. No.: 754,557

[22] Filed: Sep. 4, 1991

[30] Foreign Application Priority Data

Sep. 11, 1990 [DK] Denmark .................... 2174/90

[51] Int. Cl.$^5$ ................................................ C07C 2/00
[52] U.S. Cl. ........................................ 585/419; 585/407; 502/80; 502/84
[58] Field of Search ................ 585/407, 419; 502/84, 502/80

[56] References Cited

U.S. PATENT DOCUMENTS

| | | | |
|---|---|---|---|
| 2,401,334 | 6/1946 | Burk et al. ................... | 585/407 |
| 2,474,214 | 6/1949 | Black .......................... | 585/407 |
| 3,686,341 | 8/1972 | Eberly, Jr. .................. | 585/421 |
| 4,126,580 | 11/1978 | Lauder ......................... | 502/306 |
| 4,476,324 | 10/1984 | Reichle ........................ | 502/171 |
| 4,656,156 | 4/1987 | Misna ........................... | 502/415 |
| 4,675,307 | 6/1987 | Taniguchi et al. ........... | 502/306 |
| 4,843,168 | 6/1989 | Drezdzon et al. ........... | 585/440 |

OTHER PUBLICATIONS

Reichle, W. T., "Catalytic Reactions by Thermally Activated, Synthetic, Anionic Clay . . . ", J. Catal. 94 547-557 (1985).

*Primary Examiner*—Asok Pal
*Assistant Examiner*—P. Achutamurthy

*Attorney, Agent, or Firm*—Ostrolenk, Faber, Gerb & Soffen

[57] ABSTRACT

A process for preparing aromatic compounds, wherein a gaseous feed containing $C_6$ to $C_{20}$ hydrocarbons is reacted in the presence of a catalyst, which catalyst comprises as its catalytically active component a hydrotalcite-type material having in its uncalcined state the general formula $$Me'(II)_zMe(II)_xMe(III)_y(CO_3)(OH)_{2(x+z)+3y-2}\cdot aq$$

with an X-ray diffraction (d003) greater than about 7.4 Angstroms, and wherein

Me'(II) is at least one divalent metal selected from the Group comprising platinum, palladium, silver, ruthenium and iridium;

ME(II) is at least one divalent metal selected from the Group comprising copper, cobalt, magnesium, manganese, nickel and zinc;

ME(III) is at least one trivalent metal selected from the Group comprising aluminum, chromium and iron; and x, y and z are positive numbers satisfying the following relationships:

$(x+z)/y \geq 0.5$;

$0 < z/y \leq 3$; and $x \geq 0$.

5 Claims, No Drawings

PROCESS AND CATALYST FOR PREPARING AROMATIC COMPOUNDS

The present invention relates to the preparation of aromatic compounds by reacting gaseous feed containing $C_6$ to $C_{20}$ hydrocarbons in the presence of a catalyst.

In particular the present invention involves a novel hydrotalcite-type catalyst.

Presently most used aromatization catalysts are metal oxides, usually chromia, deposited on alumina and reduced metals of Group VIII in the Periodic Table supported on alumina, silica or activated carbon.

Other catalysts have been suggested in the art. Zeolitic aromatization catalysts loaded with a Group VIII metal are mentioned in U.S. Pat. No. 4,104,320; U.S. Pat. No. 4,448,891 and U.S. Pat. No. 4,822,762.

Danish Patent Application No. 89/6666 discloses a metal sulphide modified zeolite of ZSM-5 type useful as catalyst in the conversion of aliphatic hydrocarbons to aromatic compounds.

So far known, aromatization processes employing catalysts based on hydrotalcite-type materials for use in the preparation of aromatic compounds have not been recognized in the art.

Thus, an object at the present invention is to provide a process for preparing aromatic compounds, wherein a gaseous feed containing $C_6$ to $C_{20}$ hydrocarbons is reacted in the presence of a catalyst, which catalyst comprises as catalytically active material hydrotalcite-type material having in its uncalcined state the general formula

$$Me'(II)_z Me(II)_x Me(III)_y (CO_3)(OH)_{2(x+z)+3y-2} \cdot aq$$

with an x-ray diffraction (d003) greater than about 7.4 Angstroms, and wherein

Me'(II) is at least one divalent metal selected from the Group comprising platinum, palladium, silver, ruthenium and iridium;

ME(II) is at least one divalent metal selected from the Group comprising copper, magnesium, manganese, zinc, cobalt, nickel and iron;

ME(III) is at least one trivalent metal selected from the Group comprising aluminum, chromium and iron; and x, y and z are positive numbers satisfying the following relationship:

$(x+z)/y \geq 0.5$;

$0 < z/y \leq 3$; and $x \geq 0$

Suitably, Me(II) is magnesium, Me'(II) is palladium, platinum, or combinations thereof, Me(III) is aluminum, y is 2, and z is between about 0.0001 and 2, more specifically, between about 0.001 and 0.1.

Hydrotalcite-type materials belong to the Group of anionic clay minerals having the general formula as briefly stated herein before.

The structure of these minerals is composed of infinite layers with positively charged metal oxide-hydroxide layers with alternating interlayers of water and carbonate ions. In the metal oxide-hydroxide layers a part of the divalent metal ions is replaced by trivalent metal ions gaining positive charge, which is compensated for by the interstitially carbonate and hydroxide ions.

The hydrotalcite-type materials of this invention may be prepared by a coprecipitation procedure, in which an aqueous solution containing metals selected from the Group comprising platinum, palladium, silver, ruthenium and iridium, is combined with a solution containing divalent and trivalent metals as defined above, and precipitated with an aqueous solution of alkali metal hydroxide and alkali metal carbonate and/or alkali metal hydrogen carbonate at a pH value of between about 7.0 and about 10.0 and a temperature from about 20° C. to 80° C.

Metal Me'(II) salts are combined with divalent metal ME(II) salts including copper, manganese, zinc, cobalt, nickel, iron and magnesium, and trivalent metal Me(III) salts, including chromium, iron and aluminum salts in an aqueous solution, and coprecipitated as described above.

Suitable salts of metals are those, which upon heating to about 400° C. give the oxides of the metals, such as chlorides, nitrates and other simple salts.

Preferred salts of the divalent and trivalent metals, ME(II) and Me(III), are their nitrates.

Preferred salts of platinum and palladium are coordinated salts, such as the aminoacetates, tetrammine chlorides or tetrammine nitrates.

The molar ratio Me(II)+Me'(II)/Me(III) i.e., $(x+z)/y$, is, thereby, $\geq 0.5$, preferably between about 0.5 and 20.

Convenient amounts of Me'(II) metal in the catalyst will range between about 0.01 to about 10 per cent by weight (wt %) of the total weight of the material, preferably between about 0.1 to about 5 wt %, and most preferred between about 0.1 to about 2 wt %.

The amount and concentration of the alkali metal carbonate solution should at least contain an amount of carbonate ion, which meets the stoichiometry of the structure of the desired hydrotalcite-type material.

Following the precipitation, the obtained crystalline products are washed with water to remove excess of ions derived from the starting materials.

The X-ray diagrams of the dried and uncalcined hydrotalcite-type products, in which the products have by way of example the composition

$$Pd_{0.062}Mg_{10.4}Al_2(OH)_{24.92}CO_3 \cdot 4H_2O$$

are summarized in Table 1 below and indicate a layered structure similar to that of hydrotalcite clay $MgAl_2(OH)_{16}CO_3 \cdot 4H_2O$.

TABLE 1

| $Pd_{0.062}Mg_{10.4}Al_2(OH)_{24.92}CO_3 \cdot 4H_2O$ | | $Mg_6Al_2(OH)_{16}CO_3 \cdot 4H_2O$ | |
|---|---|---|---|
| d/Å | I/Io | d/Å | I/Io |
| 7.53 | 100 | 7.84 | 100 |
| 3.77 | 83 | 3.90 | 60 |
| 2.55 | 85 | 2.60 | 40 |
| 2.27 | 31 | 2.33 | 25 |
| 1.93 | 44 | 1.99 | 30 |
| 1.49 | 27 | 1.54 | 35 |
| 1.45 | 20 | 1.50 | 25 |
| | | 1.42 | 8 |

Even though there are some variations in the X-ray powder diffraction patterns of the hydrocalcite-type materials, certain lines in the diffraction patterns are characteristic for these materials.

The characteristic lines are shown in Table 2:

TABLE 2

| d/Å | I/Io |
| --- | --- |
| >7.4 | vs |
| >3.7 | S |
| 2.59 ± 0.1 | S |
| 2.30 ± 0.05 | M |
| 1.96 ± 0.05 | mW |

Calcination of the obtained hydrotalcite-type materials leads to substantially homogeneous metal oxide-hydroxide mixtures with a higher surface area than the uncalcined hydrotalcite-type materials.

The temperature during the calcination step has to be chosen carefully. High temperatures leading to separate phases of metal oxides and spinels have to be avoided. The X-ray diagrams of the materials calcined at the appropriate temperature do not contain any lines for formed spinels.

When used as catalyst in the inventive process the above obtained materials are activated in a hydrogen containing atmosphere at a temperature of between about 100°-450° C.

The process of the present invention is accomplished by contacting a hydrocarbon feedstream, comprising $C_6$-$C_{20}$ paraffinic hydrocarbons, with the catalyst as defined above. The catalyst is, thereby, arranged in a reaction zone, such as a fixed bed reactor or a fluidized bed reactor.

The process may be carried out at a temperature of between 100°-600° C., preferably of about 350°-500° C. The reaction can take place at a pressure of 0-100 bar, preferably about 0-10 bar, and a weight space velocity (WSHV) of about 0.01 to 200, preferably 0.01 to 10, depending on the amount and shape of the catalyst.

The catalyst may be composed with a matrix binder, such as clays, alumina, silica, titania, magnesia or compositions thereof and can be employed in any shape, such as particles, pellets or pressed tablets. In large reactor units, it might be preferred to use the catalyst loaded on monolithic structures, known in the art.

In the reaction zone the feedstream is converted to aromatic compounds at a conversion level of about 10% to about 100% per pass depending on the weight space velocity of the feedstream.

Produced aromatic compounds and non-aromatizable by-products ($C_1$-$C_5$ hydrocarbons) are recovered from the effluent of the reaction zone. Unconverted hydrocarbon feed together with converted hydrocarbons comprising paraffins, olefins and naphtenes (PON) are recycled back to the reaction zone.

The above aspects and features of the present invention are further illustrated by the following non-limiting Examples.

EXAMPLE 1

Preparation of a $Pd_{0.062}Mg_{10.4}Al_2(OH)_{24.92}CO_3.4$-$H_2O$ hydrotalcite catalyst.

A stirred solution of 112 g KOH and 10.4 g $K_2CO_3$ in 1000 ml distilled water was saturated with $CO_2$ by continously passing a stream of $CO_2$ at ambient temperature through the solution. After about 30 min. traversal of $CO_2$ is stopped and 1.5 g $Pd(NH_3)_4(NO_3)_2$ were added to the solution. The solution was stirred until all $Pd(NH_3)_4(NO_3)_2$ was dissolved.

To the stirred solution 217.6 Mg $(NO_3)_2.6H_2O$ and 56.3 g $Al(NO_3)_3.9H_2O$ in 1000 ml water were added.

The resulting slurry was kept at ambient temperature for about 18 hours, giving a final pH of 6.5.

A solid product was separated by filtration and washed with distilled water. The product was then added to a stirred solution of 30 g $KHCO_3$ in 1 l water.

The resulting slurry was heated to 65° C. for 72 hours with stirring, giving a final pH of 8.5.

A solid crystalline product, having an X-ray powder diffraction pattern as shown in Table 1 hereinbefore and chemical analysis values as summarized below, was recovered by filtration, washing with water and drying at 80° C. for 16 hours.

Chemical analysis: 28.6 wt % Mg, 6.1 wt % Al, 0.75 wt % Pd. Molar ratio Mg/Al=5.21.

EXAMPLE 2

Preparation of a Bauxite-Pd comparison catalyst. The catalyst was prepared by a similar procedure to that of Example 1 without $KHCO_3$ treatment.

X-ray diffraction analysis of the obtained product shows a Bauxite-like structure.

X-ray diffraction:

| d/Å | I/Io |
| --- | --- |
| 4.8 | 85 |
| 4.34 | 70 |
| 3.82 | 45 |
| 3.21 | 20 |
| 2.41 | 100 |
| 1.91 | 60 |
| 1.46 | 35 |

Chemical analysis: 30 wt % Mg, 6.4 wt % Al, 0.75 wt % Pd. Molar ratio Mg/Al=5.21.

EXAMPLE 3

Conversion of n-hexane to aromatic compounds by use of hydrotalcite-type catalyst according to the invention.

The catalyst of Example 1 was calcined at 500° C. for 4 hours. In the X-ray powder diffraction pattern of the calcined catalyst, no lines for formed spinel were found.

The catalyst was crushed to particles with a particle size of about 0.15-0.71 mm (25-100 Mesh) and activated in hydrogen atmosphere at 120° C. for about 30 min., followed by calcination in a hydrogen atmosphere at 425° C. for about 2 hours.

2 g of the activated catalyst were loaded in a quartz tube reactor with an inner diameter of 6 mm.

Feed gas consisting of hydrogen and n-hexane in a molar ratio of 6 was passed through the reactor.

Aromatic compounds together with non-aromatizable $C_1$-$C_5$-hydrocarbons were recovered from the reactor effluent. Unconverted feed and converted hydrocarbons comprising paraffins, olefins and naphtenes (PON), were recycled to the reactor inlet.

The process parameters used and the results obtained by the process are summarized in Table 3, which follows.

EXAMPLE 4

Conversion of n-hexane to aromatic compounds by use of a Bauxite-Pd comparison catalyst.

The comparison catalyst of Example 2 was calcined and activated as described above in Example 3.

The process was carried out by using the comparison catalyst in a similar procedure to that of Example 3.

The results obtained and process parameters used in this process are summarized in Table 3 below.

TABLE 3

| Example No. | 3 | 4 |
|---|---|---|
| Catalyst, Example No. | 1 | 2 |
| On stream Time, hr | 2 | 2 |
| Feed | $H_2/C_6H_{14}$ | $H_2/C_6H_{14}$ |
| $H_2/C_6H_{14}$, mole ratio | 6 | 6 |
| WHSV $C_6H_{14}$ | 2.11 | 2.11 |
| Temp. deg. C | 475 | 475 |
| Conversion, % | 36.70 | 29.09 |
| Product Conversion/ Feed Free Basis wt. % | | |
| $C_1$–$C_5$ | 13.27 | 17.17 |
| $C_2$–$C_4$ | 3.07 | 2.99 |
| $C_6$ + PON | 26.15 | 24.13 |
| Aromatics | 57.52 | 55.71 |
| Selectivity, % Aromatics | 77.88 | 73.43 |
| Yield, % Aromatics | 21.11 | 16.21 |

The product selectivity for aromatic compounds was calculated on the amount of converted hydrocarbon in the not recycled product stream, by dividing the fractional conversion of the feed to aromatics including benzene, toluene and xylenes, with the total amount of hydrocarbons in the product stream.

As apparent from the above result an improved selectivity and yield for aromatic compounds are obtained by use of the hydrocalcite-type catalyst according to the invention. In comparison with the Bauxite-like catalyst the selectivity is improved by about 6% and the yield of aromatics by about 30%.

We claim:

1. A process for preparing aromatic compounds, wherein a gaseous feed containing $C_6$ to $C_{20}$ hydrocarbons is reacted, under reaction conditions, in the presence of a catalyst, which catalyst has as its catalytically active component a calcined material having in its uncalcined state a hydrotalcite-type crystal structure and the general formula $$Me'(II)_zMe(II)_xMe(III)_y(CO_3)(OH)_{2(x+z)+3y-2}\cdot aq$$

with an X-ray diffraction exhibiting the following characteristic lines:

| d/Å | I/Io |
|---|---|
| >7.4 | VS |
| >3.7 | S |
| 2.59 ± 0.1 | S |
| 2.30 ± 0.05 | M |
| 1.96 ± 0.05 | mW | and wherein

Me'(II) is at least one divalent metal selected from the group consisting of platinum, palladium, silver, ruthenium and iridium;

Me(II) is at least one divalent metal selected from the group consisting of copper, cobalt, magnesium, manganese, nickel and zinc;

Me(III) is at least one trivalent metal selected from the group consisting of aluminum, chromium and iron; and x, y and z are positive numbers satisfying the following relationships:

$(x+z)/y$ is between about 0.5 and 20;

$0 < z/y \leq 3$;

z is between about 0.0001 and 2; and y=2.

2. The process of claim 1, wherein Me'(II) is selected from the Group consisting of palladium, platinum and combinations thereof.

3. The process of claim 1, wherein Me(II) is magnesium and Me(III) is aluminum.

4. The process of claim 3, wherein z is between about 0.001 and 0.1.

5. The process of claim 1 wherein said catalytically active component is $Pd_{0.062}Mg_{10.4}Al_2(OH)_{24.92}CO_3\cdot 4H_2O$.

* * * * *